United States Patent
Asano et al.

(10) Patent No.: US 7,364,728 B2
(45) Date of Patent: Apr. 29, 2008

(54) RECOMBINANT ORGANISMS PRODUCING INSECT TOXINS AND METHODS FOR CONSTRUCTING SAME

(75) Inventors: Shin-ichiro Asano, Sapporo (JP); Mikiko Nozawa, Sapporo (JP); Hisanori Bando, Sapporo (JP)

(73) Assignee: Phyllom LLC, Mountain View, CA (US)

( * ) Notice: Subject to any disclaimer, the term of this patent is extended or adjusted under 35 U.S.C. 154(b) by 170 days.

(21) Appl. No.: 11/070,575

(22) Filed: Mar. 1, 2005

(65) Prior Publication Data

US 2005/0271642 A1 Dec. 8, 2005

Related U.S. Application Data

(60) Provisional application No. 60/549,094, filed on Mar. 1, 2004.

(51) Int. Cl.
  *A01N 63/00* (2006.01)
  *A01N 25/00* (2006.01)
  *C12N 1/12* (2006.01)
  *C12N 1/20* (2006.01)
  *C07H 21/04* (2006.01)

(52) U.S. Cl. ............... 424/93.2; 424/405; 424/93.461; 435/252.1; 435/252.3; 536/23.71

(58) Field of Classification Search ................ None
See application file for complete search history.

(56) References Cited

U.S. PATENT DOCUMENTS 6,204,057 B1 * 3/2001 Schnetter et al. ........... 435/418

* cited by examiner

*Primary Examiner*—Joseph Woitach
*Assistant Examiner*—Ileana Popa
(74) *Attorney, Agent, or Firm*—Morrison & Foerster LLP

(57) ABSTRACT

This invention is a method for constructing recombinant organisms that produce proteins lethal to the larvae of insects. Nucleotide sequences were isolated from *Bacillus popilliae* that encode two adjacent, putative genes; orf1 and cryhime1. The cryhime1 sequence was related to other *Bacillus popilliae* genes that encode proteins active against Scarabaeidae insect larvae. When these nucleotide sequences were transferred to *Bacillus thuringiensis*, a protein was produced that had a lethal effect on the larvae from Scarabaeidae insects. When the orf1 sequence was removed from the recombinant *Bacillus thuringiensis* strain, no protein active against Scarabaeidae insect larvae was produced, strongly suggesting that the orf1 sequences are required for expression of the cryhime1 gene.

7 Claims, No Drawings

US 7,364,728 B2

RECOMBINANT ORGANISMS PRODUCING INSECT TOXINS AND METHODS FOR CONSTRUCTING SAME

CROSS-REFERENCE TO RELATED APPLICATIONS

This application claims priority to No. 60/549,094 filed on Mar. 1, 2004, which is hereby incorporated by reference in its entirety.

STATEMENT REGARDING FEDERALLY SPONSORED RESEARCH OR DEVELOPMENT

Not applicable.

FIELD OF THE INVENTION

The invention relates to method for constructing recombinant organisms expressing proteins useful in controlling plant pests.

BACKGROUND

The larvae of Scarabaeidae beetles (grubs) cause significant damage to a variety of crops and ornamental plantings in the United States. The Japanese beetle, a species of this insect family, is one of the most significant of these pests with respect to ornamental lawns and turf grass. Adult insects lay their eggs in turf, with the resulting grubs feeding on the roots and subsequently destroying the plant. Severe infestations of the grubs can destroy entire lawns due to the continuing increases in numbers of grubs from year to year. One thousand Japanese beetles can lay eggs for 50,000 grubs. In the case of Japanese beetles the damage is then greatly extended due to the fact that the adults feed on a wide variety of agricultural and ornamental plants including fruit trees, grape vines, and roses.

Milky disease is a natural disease of Scarabaeidae beetles, caused by the bacterium *Bacillus popilliae*. It's called Milky disease because of the white appearance of the grubs, created by a large number of bacterial spores in the hemolymph or insect blood. To characterize the mode of action of *Bacillus popilliae* on Scarabaeidae larvae, several genes encoding proteins toxic to the larvae of Scarabaeidae insects have been isolated from *Bacillus popilliae* strains (*J. Bacteriol.* 179, 4336-4341 (1997); U.S. patent application 20020182693, herein incorporated by reference). In this application, we describe a novel *Bacillus popilliae* gene, cryhime1 (SEQ ID NO:4), that encodes a protein active against Scarabaeidae larvae.

The relationship between *Bacillus popilliae* and milky disease has been exploited to produce an effective biopesticide made from a spore powder of *Bacillus popilliae*. When compared with other biopesticides made from other Bacilli such as *Bacillus thuringiensis*, however, *Bacillus popilliae* biopesticides are extremely costly. Unlike *Bacillus thuringiensis*, *Bacillus popilliae* sporulation has not been achieved in vitro, so biopesticides made from *Bacillus popilliae* spore preparations are produced commercially in vivo by injecting the larvae with bacterial cells. The larvae are incubated until they develop a milky appearance, and then crushed and dried to give a spore powder.

By using *Bacillus thuringiensis* in place of *Bacillus popilliae*, significant advantages are realized. In addition to reduced cost as described above, other advantages include the fact that *Bacillus thuringiensis* is better characterized than *Bacillus popilliae* (i.e., many different strains and tools for *Bacillus thuringiensis* are available to achieve maximal biopesticide production) and *Bacillus thuringiensis* does not harbor vancomycin-resistance genes as do some *Bacillus popilliae* strains (*Antimicrob. Agents Chemother.* 44(3), 705-709, 2000). Vancomycin-resistance genes could be transferred to bacterial pathogens of humans from the sustained presence of *Bacillus popilliae* spores in the environment. In fact, it has been suggested that clinical isolates of *Enterococcus facealis* acquired vancomycin resistance by the transfer of a gene cluster from *Bacillus popilliae* spores (*Antimicrob. Agents Chemother.* 44(3), 705-709, 2000).

For these reasons, it is desirable to produce a *Bacillus thuringiensis* biopesticide that is toxic to Scarabaeidae larvae.

SUMMARY OF THE INVENTION

The present invention addresses the aforementioned needs by providing a method that renders expression of a *Bacillus popilliae* crystal protein in *Bacillus thuringiunsis* that is toxic to Scarabaeidae larvae. The resulting *Bacillus thuringiensis* strain is useful as a biopesticide. The method involves the transfer of two novel *Bacillus popilhias* polyncleotide sequences to *Bacillus thuringiensis*. One novel polynucleotide sequence, SEQ ID NO:4, encodes a protein, SEQ ID NO: 6, active against the larvae of Scarabaeidae insects. The second novel polynucleotide sequence, SEQ ID NO:3, encodes the protein of SEQ ID NO:5, which enables the expression of the Scarabaeidae-active protein in *Bacillus thuringiensis*.

In one embodiment of the invention, isolated nucleic acid molecules and the proteins they encode are provided. In another embodiment, vectors comprising said isolated nucleic molecules are provided.

In yet another embodiment, recombinant *Bacillus thuringiensis* microorganisms containing said isolated nucleic acid molecules and proteins, are provided.

DETAILED DESCRIPTION OF THE INVENTION

I. Introduction

The present invention provides a method that enables expression of a novel *Bacillus popilliae* crystal protein insect toxin in *Bacillus thuringiensis*. The resulting *Bacillus thuringiensis* strain is useful as a biopesticide. The method involves the transfer of two novel *Bacillus popilliae* polynucleotide sequences to *Bacillus thuringiensis*; the two aforementioned polynucleotide sequences are a part of the present invention. One novel polynucleotide sequence, SEQ ID NO:4, encodes a protein (SEQ ID NO: 6) active against the larvae of Scarabaeidae insects, said protein a part of the present invention. The second novel polynucleotide sequence, SEQ ID NO:3, encodes a protein (SEQ ID NO:5), which enables the expression of the Scarabaeidae-active protein in *Bacillus thuringiensis*, said protein also a part of the present invention. SEQ ID NO:3 , or a polynucleotide sequence substantially the same as SEQ ID NO:3, is necessary for the expression of the Scarabaeidae-active protein of *Bacillus popilliae* in *Bacillus thuringiensis*.

The present invention provides a method that enables expression of a novel *Bacillus popilliae* crystal protein insect toxin in *Bacillus thuringiensis*. The resulting *Bacillus thuringiensis* strain is useful as a biopesticide. The method involves the transfer of two novel *Bacillus popilliae* polynucleotide sequences to *Bacillus thuringiensis*; the two aforementioned polynucleotide sequences are a part of the present invention. One novel polynucleotide sequence, SEQ ID NO:4, encodes a protein (SEQ ID NO: 6) active against the larvae of Scarabaeidae insects, said protein a part of the present invention, The second novel polynucleotide sequence, SEQ ID NO:3, encodes a protein (SEQ ID NO:5), which enables the expression of the Scarabaeidae-active protein in *Bacillus thuringiensis*, said protein also a part of the present invention. SEQ ID NO:3, or a polynucleotide sequence substantially the same as SEQ ID NO:3, is necessary for the expression of the Scarabaeidae-active protein of *Bacillus popilliae* in *Bacillus thuringiensis*.

The polypeptides of the present invention may include polypeptides containing substitutions, deletions or insertions of one or several numbers of amino acid residues as long as the polypeptides retain the activity of the exemplified proteins. Here, the term "several numbers of" means a number of from 2 to 100, preferably from 2 to 50, and more preferably from 2 to 9, although it may vary depending on the position and kinds of amino acid residues in a three-dimensional structure of the polypeptide. These polypeptides, including substitutions, deletions or insertions of one or several numbers of amino acid residues can be obtained, for example, by introducing a mutation to a polynucleotide encoding the polypeptide by site-specific mutagenesis and performing transcription and translation of the polynucleotide, as is well known to the skilled artisan. Fragments and equivalents which retain the activity of the exemplified proteins would be within the scope of the present invention.

The present invention is further directed to isolated nucleic acid molecules comprising nucleotide sequences that encode proteins, wherein said nucleotide sequences comprise a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of SEQ ID NO:3 or SEQ ID NO:4.

The present invention is still further directed to one or more recombinant *Bacillus thuringiensis* microorganisms containing the *Bacillus popilliae* cryhime1 gene (SEQ ID NO:4) in combination with the novel *Bacillus popilliae* orf1 gene (SEQ ID NO:3).

In the present invention, we describe a method for expressing a *Bacillus popilliae* protein in *Bacillus thuringiensis* that is lethal to Scarabaeidae insects. No previous reports have shown expression of *Bacillus popilliae* insecticidal genes in *Bacillus thuringiensis*. The method of the invention involves the requirement of novel nucleic acid sequences from *Bacillus popilliae* called orf1 (SEQ ID NO:3) for expression of a *Bacillus popilliae* insecticidal gene (SEQ ID NO:4) in *Bacillus thuringiensis*. When the sequences from orf1 were placed on a plasmid containing the *Bacillus popilliae* cryhime1 gene (SEQ ID NO:4) and transferred to *Bacillus thuringiensis*, large bipyramidal crystals and substantial 150 kDa protein were produced, and the resulting recombinant *Bacillus thuringiensis* strain was lethal to Scarabaeidae larvae. When the orf1 sequences were removed from the plasmid, no bipyramidal crystals or 150 kDa protein were observed and the resulting *Bacillus thuringiensis* strain was not lethal to Scarabaeidae larvae, suggesting that the orf1 sequences were essential for expression of the insecticidal cryhime1 gene in *Bacillus thuringiensis*.

In the present invention, the sequences encoding orf1 and the insecticidal protein, cryhime1, were isolated from a *Bacillus popilliae* strain. However, the method of this invention also could be used with sequences related to orf1 isolated from other *Bacillus* species and with *Bacillus* genes encoding toxins active against a variety of pests.

II. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); and Short Protocols in Molecular Biology (Wiley and Sons, 1999). Furthermore, procedures employing commercially available assay kits and reagents will typically be used according to manufacturer-defined protocols unless otherwise noted.

III. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

As used herein, "cry gene" is a gene that encodes an insecticidal crystal toxin.

By "Cry protein" is meant an insecticidal crystal toxin.

By "activity" of the crystal protein is meant the protein's function as an orally active insect control agent, especially its ability to disrupt or deter insect feeding, which may or may not cause death of the insect. When a protein of the invention is delivered to the insect, the result is typically death of the insect, or the insect does not feed upon the source that makes the protein available to the insect.

"Associated with" refers to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A "chimeric gene" is a recombinant nucleic acid sequence in which one nucleic acid sequence is operatively linked to, or associated with, a second nucleic acid sequence where the two nucleic acid sequences are not normally operatively linked in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a protein means that the protein comes in contact with an insect, resulting in a toxic effect and control of the insect. The protein can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Insecticidal" is defined as a toxic biological activity capable of controlling insects, preferably by killing them.

An "isolated nucleic acid molecule" or an "isolated protein" is a nucleic acid molecule or protein that, by the hand of man, exists apart from its native environment and is therefore not a product of nature. An isolated nucleic acid molecule or protein may exist in a purified form or may exist in a non-native environment such as, for example, a recombinant host cell. The terms "polynucleotide" and "nucleic acid molecule" are used interchangeably herein. The terms "protein" and "polypeptide" also are used interchangeably herein.

By "DNA" is meant a polymeric form of deoxyribonucleotides (adenine, guanine, thymine, or cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. The term captures molecules that include the four bases adenine, guanine, thymine, or cytosine, as well as molecules that include base analogs which are known in the art.

A "nucleic acid molecule" or "nucleic acid sequence" refers to a DNA or RNA molecule or sequence. The term captures molecules or sequences that include any of the known base analogues of DNA and RNA such as, but not limited to 4-acetylcytosine, 8-hydroxy-$N^6$-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-$N^6$-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A nucleic acid molecule or sequence may be isolated from any source.

"ORF" means open reading frame.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of higher organized unit such as, for example, plant tissue, a plant organ, or a whole plant.

By "introducing a polynucleotide" or "introducing a nucleotide sequence" or "introducing a gene" is meant any process or technique known in the art such as transduction, transformation, electroporation and the like for introducing a heterologous nucleic acid molecule into a host cell or organism.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct in which the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

By "vector" is meant any genetic element, such as a plasmid, phage, transposon, cosmid, chromosome, virus, virion, etc., which is capable of replication or expressing a heterologous gene or genes when associated with the proper control elements and which can transfer gene sequences between cells. Thus, the term includes cloning and expression vehicles, as well as viral vectors.

"Transformed/transgenic/recombinant" refers to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof.

A "non-transformed", "non-transgenic", or "non-recombinant" host refers to a wild-type organism, e.g., a bacterium or plant, which does not contain the heterologous nucleic acid molecule.

As used herein, "variant" genes have nucleotide sequences which encode the same proteins or which encode proteins having activities equivalent to an exemplified protein.

By "equivalent proteins" is meant proteins having the same, essentially the same, or substantially the same biological activity as the exemplified proteins.

As used herein, "essentially the same" or "substantially the same" sequence refers to sequences which have amino acid substitutions, deletions, additions, or insertions which do not materially affect activity.

IV. Methods and Uses of the Present Invention

It should be apparent to a person skilled in the art of the present invention that genes encoding proteins according to the subject invention can be obtained through several means. These genes of the subject invention can be constructed synthetically, for example, by the use of a gene synthesizer. Because of the redundancy of the genetic code, a variety of different DNA sequences can encode the amino acid sequences disclosed herein. It is well within the skill of a person trained in the art to create these alternative DNA sequences encoding the same, essentially the same, or substantially the same proteins. These variant DNA sequences are within the scope of the subject invention. "Synthetic" refers to a nucleic acid molecule comprising structural characteristics that are not present in the natural molecule. For example, an artificial sequence that resembles more closely the G+C content and the normal codon distribution of dicot and/or monocot genes is said to be synthetic.

As the skilled artisan would readily recognize, DNA typically exists in a double-stranded form. In this arrangement, each strand is complementary to the other strand. As DNA is replicated in a bacterium, for example, additional, complementary strands of DNA are produced. Thus, the present invention includes the use of the exemplified nucleic acid molecules shown in the attached sequence listing and/or the complementary strands. RNA and PNA (peptide nucleic acids) that are functionally equivalent to the exemplified DNA are included in the subject invention.

The toxins and genes of the subject invention can be further defined by their amino acid and nucleic acid sequences. The sequences of the molecules within each novel class can be identified and defined in terms of their similarity or identity to certain exemplified sequences as well as in terms of the ability to hybridize with, or be amplified by, certain exemplified probes and primers.

Two proteins of the present invention have been specifically provided in SEQ ID NO:5 and SEQ ID NO:6. Since these proteins are merely exemplary of the proteins of the present invention, it should be readily apparent that the present invention comprises variant or equivalent proteins (and nucleic acid sequences coding for equivalent proteins) having the same or similar activity of the exemplified proteins. An equivalent protein will have amino acid similarity (and/or homology) with an exemplified protein. The amino acid identity will typically be greater than 60%, preferably greater than 75%, more preferably greater than 80%, even more preferably greater than 90%, and can be greater than 95%. Preferred polynucleotides and proteins of the subject invention also can be defined in terms of more particular identity and/or similarity ranges. For example, the identity and/or similarity can be 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, word length=12, to obtain nucleotide sequences with the desired percent sequence identity. To obtain gapped alignments for comparison purposes, Gapped BLAST is used as described in Altschul et al. (1997), *Nucl. Acids Res.* 25:3389-3402. When utilizing BLAST and Gapped BLAST programs, the default parameters of the respective programs (NBLAST and XBLAST) are used. See http://www.ncbi.nih.gov.

Additional polynucleotides of the present invention can be identified and defined in terms of their similarity or identity to the sequences of SEQ ID NO:3 and SEQ ID NO:4. The genes and proteins of the present invention also can be defined in terms of the ability to hybridize with, or be amplified by, certain nucleic acid sequences. The polynucleotides of the present invention include those that are hybridizable under stringent conditions to each of the above-mentioned polynucleotides or a probe that can be prepared from the above-mentioned polynucleotides as far as they encode polypeptides having an insecticidal effect on a Scarabaeidae insect or polypeptides that facilitate expression of Scarabaeidae-active proteins. The term "stringent conditions" used herein refers to a condition under which a so-called specific hybrid is formed and nonspecific hybrid is not formed. Specifically, it includes a condition of 65° C., 2×SSC (1×SSC is 0.15 M NaCl, 15 mM Sodium Citrate, pH 7.0) and 0.1% SDS (Sodium Dodecyl Sulfate). The classes of toxins provided herein can also be identified based on their immunoreactivity with certain antibodies.

In a particularly preferred embodiment, the present invention is directed to a method for expression of an isolated nucleic acid molecule comprising a nucleic acid sequence that encodes a Scarabaeidae-active *Bacillus popilliae* protein, wherein the nucleic acid sequence is SEQ ID NO:4. In this embodiment, the presence of a second nucleic acid sequence of SEQ ID NO:3 is required for efficient expression of the protein encoded by SEQ ID NO:4.

Also embodied are polynucleotides isolated from other *Bacillus popilliae* strains that encode proteins with activities the same as, or substantially the same as, those proteins exemplified herein. Other sources of *Bacillus popilliae* polynucleotides include, but are not limited to, *Paenibacillus lentimorbus* semadara, *Paenibacillus popilliae*, *Bacillus popilliae* semadara, FERM P-16818, *Bacillus popilliae* var. Mame, FERM P-17661, *Bacillus popilliae* var. popilliae Hime, FERM P-17660, *Bacillus popilliae* var. *popilliae* Sakura, FERM P-17662, and *Bacillus popilliae* Dutky, American Type Culture Collection No. 14706.

In another embodiment of the present invention, polynucleotides encoding Scarabaeidae-active from *Bacillus thuringiensis* strains are provided. In still another embodiment, the polypeptide of SEQ ID NO:5, or another polypeptide having the same, or substantially the same, function as the polypeptide of SEQ ID NO:5, can be used to facilitate the expression of other pesticidal genes and toxins, including, lepidopteran-active toxins. These genes and toxins can be isolated from many sources of *Bacillus thuringiensis*, including, but not limited to, *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp. *thuringiensis*, *Bacillus thuringiensis* subsp. *alesti*, *Bacillus thuringiensis* subsp. *canadiensis*, *Bacillus thuringiensis* subsp. *darmstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, *Bacillus thuringiensis* subsp. *toumanoffi*, *Bacillus thuringiensis* subsp. *pondicheriensis*, *Bacillus thuringiensis* subsp. *shandogiensis*, *Bacillus thuringiensis* subsp. *sotto*, *Bacillus thuringiensis* subsp. *nigeriae*, *Bacillus thuringiensis* subsp. *yunnanensis*, *Bacillus thuringiensis* subsp. *dakota*, *Bacillus thuringiensis* subsp. *indiana*, *Bacillus thuringiensis* subsp. *tohokuensis*, *Bacillus thuringiensis* subsp. *kumamotoensis*, *Bacillus thuringiensis* subsp. *tochigiensis*, *Bacillus thuringiensis* subsp. *thompsoni*, *Bacillus thuringiensis* subsp. *wuhanensis*, *Bacillus thuringiensis* subsp. *kyushuensis*, *Bacillus thuringiensis* subsp. *ostriniae*, *Bacillus thuringiensis* subsp. *tolworthi*, *Bacillus thuringiensis* subsp. *pakistani*, *Bacillus thuringiensis* subsp. *japonensis*, *Bacillus thuringiensis* subsp. *colmeri*, *Bacillus thuringiensis* subsp. *pondicheriensis*, *Bacillus thuringiensis* subsp. *shandongiensis*, *Bacillus thuringiensis* subsp. *neoleonensis*, *Bacillus thuringiensis* subsp. *coreanensis*, *Bacillus thuringiensis* subsp. *silo*, *Bacillus thuringiensis* subsp. *mexicanensis*, *Bacillus thuringiensis* subsp. *israelensis*, *Bacillus thuringiensis* subsp. *berliner*, *Bacillus thuringiensis* subsp. *cameroun*, *Bacillus thuringiensis* subsp. *ongbei*, *Bacillus thuringiensis* subsp. *fukuokaensis*, *Bacillus thuringiensis* subsp. *higo*, *Bacillus thuringiensis* subsp. *japonensis* Buibui, *Bacillus thuringiensis* subsp. *jegathesan*, *Bacillus thuringiensis* subsp. *kenyae*, *Bacillus thuringiensis* subsp. *kunthala*, *Bacillus thuringiensis* subsp. *medellin*, *Bacillus thuringiensis* subsp. *roskildiensis*, *Bacillus thuringiensis* subsp. *san diego*, *Bacillus thuringiensis* subsp. *shanghai*, *Bacillus thuringiensis* subsp. *sotto*, *Bacillus thuringiensis* subsp. *tenebrionis*, and *Bacillus thuringiensis* subsp. *thompsoni*.

In one embodiment of the present invention, the polypeptide of SEQ ID NO:5, or another polypeptide having the same, or substantially the same function, as the polypeptide of SEQ ID NO:5, can be used to facilitate the expression of other pesticidal toxins. Other pesticidal toxins can be, but are not limited to, the following (see also http://www.biols.susx.ac.uk/home/Neil_Crickmore/Bt/toxins2.html):

Cry1Aa1, Cry1Aa2, Cry1Aa3, Cry1Aa4, Cry1Aa5, Cry1Aa6, Cry1Aa7, Cry1Aa8, Cry1Aa9, Cry1Aa10, Cry1Aa11, Cry1Aa12, Cry1Aa13, Cry1Aa14, Cry1Ab1, Cry1Ab2, Cry1Ab3, Cry1Ab4, Cry1Ab5, Cry1Ab6, Cry1Ab7, Cry1Ab8, Cry1Ab9, Cry1Ab10, Cry1Ab11, Cry1Ab12, Cry1Ab13, Cry1Ab14, Cry1Ab15, Cry1Ab16, Cry1Ac1, Cry1Ac2, Cry1Ac3, Cry1Ac4, Cry1Ac5, Cry1Ac6, Cry1Ac7, Cry1Ac8, Cry1Ac9, Cry1Ac10, Cry1Ac11, Cry1Ac12, Cry1Ac13, Cry1Ac14, Cry1Ac15, Cry1Ad1, Cry1Ad2, Cry1Ae1, Cry1Af1, Cry1Ag1, Cry1Ah1, Cry1Ai1, Cry1Ba1, Cry1Ba2, Cry1Ba3, Cry1Ba4, Cry1Bb1, Cry1Bc1, Cry1Bd1, Cry1Bd2, Cry1Be1, Cry1Be2, Cry1Bf1, Cry1Bf2, Cry1Bg1, Cry1Ca1, Cry1Ca2, Cry1Ca3, Cry1Ca4, Cry1Ca5, Cry1Ca6, Cry1Ca7, Cry1Ca8, Cry1Ca9, Cry1Ca10, Cry1Cb1, Cry1Cb2, Cry1Da1, Cry1Da2, Cry1Db1, Cry1Db2, Cry1Ea1, Cry1Ea2, Cry1Ea3, Cry1Ea4, Cry1Ea5, Cry1Ea6, Cry1Eb1, Cry1Fa1, Cry1Fa2, Cry1Fb1, Cry1Fb2, Cry1Fb3, Cry1Fb4, Cry1Fb5, Cry1Ga1, Cry1Ga2, Cry1Gb1, Cry1Gb2, Cry1Gc, Cry1Ha1, Cry1Hb1, Cry1Ia1, Cry1Ia2, Cry1Ia3, Cry1Ia4, Cry1Ia5, Cry1Ia6, Cry1Ia7, Cry1Ia8, Cry1Ia9, Cry1Ia10, Cry1Ia11, Cry1Ib1, Cry1Ic1, Cry1Ic2, Cry1Id1, Cry1Ie1, Cry1If1, Cry1Ja1, Cry1Jb1, Cry1Jc1, Cry1Jc2, Cry1Jd1, Cry1Ka1, Cry2Aa1, Cry2Aa2, Cry2Aa3, Cry2Aa4, Cry2Aa5, Cry2Aa6, Cry2Aa7, Cry2Aa8, Cry2Aa9, Cry2Aa10, Cry2Aa11, Cry2Ab1, Cry2Ab2, Cry2Ab3, Cry2Ab4, Cry2Ab5, Cry2Ab6, Cry2Ac1, Cry2Ac2, Cry2Ac3, Cry2Ad1, Cry2Ae1, Cry3Aa1, Cry3Aa2, Cry3Aa3, Cry3Aa4, Cry3Aa5, Cry3Aa6, Cry3Aa7, Cry3Ba1, Cry3Ba2, Cry3Bb1, Cry3Bb2, Cry3Bb3, Cry3Ca1, Cry4Aa1, Cry4Aa2, Cry4Aa3, Cry4Ba1, Cry4Ba2, Cry4Ba3, Cry4Ba4, Cry4Ba5, Cry5Aa1, Cry5Ab1, Cry5Ac1, Cry5Ba1, Cry6Aa1, Cry6Aa2, Cry6Ba1, Cry7Aa1, Cry7Ab1, Cry7Ab2, Cry8Aa1, Cry8Ba1, Cry8Bb1, Cry8Bc1, Cry8Ca1, Cry8Ca2, Cry8Da1, Cry8Da2, Cry8Da3, Cry8Ea1, Cry9Aa1, Cry9Aa2, Cry9Ba1, Cry9Ca1, Cry9Ca2, Cry9Da1, Cry9Da2, Cry9Ea1, Cry9Ea2, Cry9Eb1, Cry9Ec1, Cry10Aa1, Cry10Aa2, Cry10Aa3, Cry11Aa1, Cry11Aa2, Cry11Aa3, Cry11Ba1, Cry11Bb1, Cry12Aa1, Cry13Aa1, Cry14Aa1, Cry15Aa1, Cry16Aa1, Cry17Aa1, Cry18Aa1, Cry18Ba1, Cry18Ca1, Cry19Aa1, Cry19Ba1, Cry20Aa1, Cry21Aa1, Cry21Aa2, Cry21Ba1, Cry22Aa1, Cry22Aa2, Cry22Ab1, Cry22Ab2, Cry22Ba1, Cry23Aa1, Cry24Aa1, Cry25Aa1, Cry26Aa1, Cry27Aa1, Cry28Aa1, Cry28Aa2, Cry29Aa1, Cry30Aa1, Cry30Ba1, Cry31Aa1, Cry31Aa2, Cry32Aa1, Cry32Ba1, Cry32Ca1, Cry32Da1, Cry33Aa1, Cry34Aa1, Cry34Aa2, Cry34Ab1, Cry34Ac1, Cry34Ac2, Cry34Ba1, Cry35Aa1, Cry35Aa2, Cry35Ab1, Cry35Ab2, Cry35Ac1, Cry35Ba1, Cry36Aa1, Cry37Aa1, Cry38Aa1, Cry39Aa1, Cry40Aa1, Cry40Ba1, Cry41Aa1, Cry41Ab1, Cry42Aa1, Cry43Aa1, Cry43Ba1, Cyt1Aa1, Cyt1Aa2, Cyt1Aa3, Cyt1Aa4, Cyt1Aa5, Cyt1Ab1, Cyt1Ba1, Cyt2Aa1, Cyt2Aa2, Cyt2Ba1, Cyt2Ba2, Cyt2Ba3, Cyt2Ba4, Cyt2Ba5, Cyt2Ba6, Cyt2Ba7, Cyt2Ba8, Cyt2Ba9, Cyt2Bb1, Cyt2Bc1, and Cyt2Ca1.

In another embodiment, the present invention provides a method of controlling insects comprising delivering to the insects an effective amount of a *Bacillus popilliae* crystal protein according to the present invention. In one embodiment, the insects are lamellicorn beetles (Scarabaeidae). In one facet of the invention, the *Bacillus popilliae* crystal protein is delivered to the insects orally.

Control of pests using the isolates, proteins and nucleic acid molecules of the subject invention can be accomplished by a variety of methods known to those skilled in the art. These methods include, for example, the application of *Bacillus thuringiensis* isolates to the pests (or their location), the application of recombinant microbes to the pests (or their locations), and the transformation of plants with genes which encode the pesticidal toxins of the subject invention. Microbes for use according to the subject invention may be, for example, *Bacillus thuringiensis*, or other *Bacillus* species. Recombinant hosts can be made by those skilled in the art using standard techniques. Materials necessary for these transformations are disclosed herein or are otherwise readily available to the skilled artisan. For example, *Bacillus thuringiensis* and *Bacillus popilliae* species and strains can be ordered from the American Type Culture Collection (www.atcc.org) or obtained from the U.S. Department of Agriculture. Suitable vectors and reagents can be obtained from a variety of sources including Stratagene (www.stratagene.com) and Invitrogen (www.invitrogen) and many other commercial suppliers as is well known to the skilled artisan.

In another embodiment, the nucleic acid sequences of the invention are introduced, for example by electroporation, into a desired host such as the *Bacillus thuringiensis* subsp. *kurstaki* cry-strain, Bt51.

In another embodiment, the present invention provides a method for expression of a pesticidal gene in a transgenic host cell using polypeptides having activity the same as, or substantially the same as, the polypeptide of SEQ ID NO:5.

A transgenic host cell according to this aspect of the present invention may be a transgenic bacterial cell. The transgenic bacterial cell may be one of the following *Bacillus* species hosts: *Bacillus megaterium; Bacillus mycoides; Bacillus* alvei; *Bacillus brevis; Bacillus circulans; Bacillus coagulans; Bacillus licheniformis; Bacillus macerans; Bacillus pumilus; Bacillus subtilis; Bacillus sphaericus; Bacillus thuringiensis* subsp. *kurstaki; Bacillus thuringiensis* subsp. *aizawai; Bacillus thuringiensis* subsp. *galleriae; Bacillus thuringiensis* subsp. *entomocidus; Bacillus thuringiensis* subsp. *tenebrionis; Bacillus thuringiensis* subsp. *thuringiensis; Bacillus thuringiensis* subsp. *alesti; Bacillus thuringiensis* subsp. *canadiensis; Bacillus thuringiensis* subsp. *darmstadiensis; Bacillus thuringiensis* subsp. *dendrolimus; Bacillus thuringiensis* subsp. *finitimus; Bacillus thuringiensis* subsp. *kenyae; Bacillus thuringiensis* subsp. *morrisoni; Bacillus thuringiensis* subsp. *subtoxicus; Bacillus thuringiensis* subsp. *toumanoffi; Bacillus thuringiensis* subsp. *pondicheriensis; Bacillus thuringiensis* subsp. *shandogiensis; Bacillus thuringiensis* subsp. *sotto; Bacillus thuringiensis* subsp. *nigeriae; Bacillus thuringiensis* subsp. *yunnanensis; Bacillus thuringiensis* subsp. *dakota; Bacillus thuringiensis* subsp. *indiana; Bacillus thuringiensis* subsp. *tohokuensis; Bacillus thuringiensis* subsp. *kumamotoensis; Bacillus thuringiensis* subsp. *tochigiensis; Bacillus thuringiensis* subsp. *thompsoni; Bacillus thuringiensis* subsp. *wuhanensis; Bacillus thuringiensis* subsp. *kyushuensis; Bacillus thuringiensis* subsp. *ostriniae; Bacillus thuringiensis* subsp. *tolworthi; Bacillus thuringiensis* subsp. *pakistani; Bacillus thuringiensis* subsp. *japonensis; Bacillus thuringiensis* subsp. *colmeri; Bacillus thuringiensis* subsp. *pondicheriensis; Bacillus thuringiensis* subsp. *shandongiensis; Bacillus thuringiensis* subsp. *neoleonensis; Bacillus thuringiensis* subsp. *coreanensis; Bacillus thuringiensis* subsp. *silo; Bacillus thuringiensis* subsp. *mexicanensis; Bacillus thuringiensis* subsp. *israelensis; Bacillus thuringiensis* subsp. *berliner; Bacillus thuringiensis* subsp. *cameroun; Bacillus thuringiensis* subsp. *ongbei; Bacillus thuringiensis* subsp. *fukuokaensis; Bacillus thuringiensis* subsp. *higo; Bacillus thuringiensis* subsp. *israelensis; Bacillus thuringiensis* subsp. *japonensis* Buibui; *Bacillus thuringiensis* subsp. *jegathesan; Bacillus thuringiensis* subsp. *kenyae; Bacillus thuringiensis* subsp. *kunthala; Bacillus thuringiensis* subsp. *medellin; Bacillus thuringiensis* subsp. *roskildiensis; Bacillus thuringiensis* subsp. *san diego; Bacillus thuringiensis* subsp. *shanghai; Bacillus thuringiensis* subsp. *sotto; Bacillus thuringiensis* subsp. *tenebrionis*; and *Bacillus thuringiensis* subsp. *thompsoni.*

A transgenic host cell according to this aspect of the present invention also may be a transgenic plant comprising a transgenic plant cell. The transgenic plant may be one of the following important crops: turf, maize, rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. In one aspect of the invention, the transgenic plant cell comprises a turf cell. The present invention also provides seed of such a transgenic plant.

In a further aspect, the present invention provides a method of producing an insect-resistant plant, comprising introducing the nucleic acid molecules of the subject invention into the plant, wherein the nucleic acid molecules are expressed in the plant in an effective amount to control insects. The insects may be lamellicorn beetles (Scarabaeidae).

According to the present invention, polypeptides having a larvae growth inhibiting or an insecticidal effect on Scarabaeidae insects are produced. The Scarabaeidae insects that are the target of control with the polypeptides of the present invention include, but are not limited to, *Anomala cuprea, Blitopertha orientalis, Popilliajaponica, Phyllopertha diversa, Adoretus tenuimaculatus, Anomala rufocuprea* and the like. The polypeptides of the present invention are effective on *Anomala cuprea, Popillia japonica*, and *Anomala daimiana.*

The compositions of the present invention may be effective against pests of the order *Lepidoptera*, for example, *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylis hospes, Colias eurytheme, Corcyra cephalonica, Cydia latiferreanus, Cydia pomonella, Datana integerrima, Dendrolimus sibericus, Desmiafuneralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma* sp., *Mamestra brassicae, Mamestra configurata, Manduca quinquemaculata, Manduca sexta, Maruca testulalis, Melanchra picta, Operophtera brunata, Orgyia* sp., *Ostrinia nubilalis, Paleacrita vernata, Papilio cresphontes, Pectinophora gossypiella, Phryganidia californica, Phylonorycter blancardella, Pieris napi, Pieris rapae, Plathypena scabra, Platynota flouendana, Platynota sultana, Platyptilia carduidactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana, Spodoptera* sp., *Syngrapha falcifera, Thaurnstopoea pityocampa, Tineola bisselliella, Trichoplusia ni, Udea rubigalis, Xylomyges curialis, Yponomeuta padella.*

The compositions of the present invention also may be effective against insect pests of the order *Coleoptera*, e.g., *Leptinotarsa* sp., *Acanthoscelides obtectus, Callosobruchus chinensis, Epilachna varivestis, Pyrrhalta luteola, Cylasformicarius elegantulus, Listronotus oregonensis, Sitophilus* sp., *Cyclocephala borealis, Cyclocephala immaculata, Macrodactylus subspinosus, Popillia japonica, Rhizotrogus* majalis, *Alphitobius diaperinus, Palorus ratzeburgi, Tenebrio molitor, Tenebrio obscurus, Tribolium castaneum, Tribolium confusum, Tribolius destructor, Diptera*, e.g., *Aedes* sp., *Andes vittatus, Anastrepha ludens, Anastrepha suspensa, Anopheles barberi, Anopheles quadrimaculatus, Armigeres subalbatus, Calliphora stygian, Calliphora vicina, Ceratitis capitata, Chironomus tentans, Chrysomya ruffacies, Cochliomyia macellaria, Culex* sp., *Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina morsitans morsitans, Glossina morsitans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria* sp., *Nephrotoma suturalis, Ophyra aenescens, Phaenicia sericata, Phlebotomus* sp., *Phormia regina, Sabethes cyaneus, Sarcophaga bullata, Scatophaga stercoraria, Stomaxys calcitrans, Toxorhynchites amboinensis, Tripteroides bambusa, Acari*, e.g., *Oligonychus pratensis, Panonychus ulmi, Tetranychus urticae, Hymenoptera*, e.g., *Iridomyrmex humilis, Solenopsis invicta, Isoptera*, e.g., *Reticulitermes hesperus, Reticulitermes flavipes, Coptotermes formosanus, Zootermopsis angusticollis, Neotermes connexus, Incisitermes minor, Incisitermes immigrans, Siphonaptera*, e.g., *Ceratophyllus gallinae, Ceratophyllus niger, Nosopsyllusfasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans*, and *Tylenchida*, e.g., *Melodidogyne incognita, Pratylenchus penetrans.*

Hereinafter, the present invention will be illustrated more specifically. However, the scope of the present invention is not limited thereto.

V. EXAMPLES

The following examples are provided to illustrate the methods and compositions of the present invention. Those skilled in the art will recognize that while specific embodiments have been illustrated and described, they are not intended to limit the invention.

Example 1

Isolation of an Insecticidal Toxin Gene

A number of *Bacillus popilliae (Paenibacillus popilliae)* strains have been isolated from field-collected Scarabaeidae beetle grubs in Japan (*Appl. Entomol. Zool.* 32, 583-588 (1997)). The insecticidal gene disclosed in this patent application was found in one of these *Bacillus popilliae* strains called *Bacillus popilliae* var *popilliae* Hime.

Plasmid DNA was purified from *Bacillus popilliae* var. *popilliae* Hime according to the method described in a paper published by Valyasevi et al. (*J. Invertebr. Pathol.* 56, 286-288 (1990). The isolated DNA was digested with EcoRI for 30 min, and digested fragments were separated by gel electrophoresis. DNA fragments in the 4-6 kb range were extracted from the gel and ligated to EcoRI-cut pBluescriptSK(−). *E. coli* cells were transformed with the ligated DNA.

The clone containing an insecticidal toxin gene was identified by colony hybridization using a PCR-amplified DNA probe and the ALKPHOS direct Amersham-Pharmacia Chemiluminescence Detection Kit. The probe was made as follows: Degenerate primers with the following sequences, orfF: 5-atccagaagtggatttacacgtgtt (SEQ ID NO:7) 5-atccagaagttaatttacacgtgtt (SEQ ID NO:8); 5-atccagaagttgattta-cacgtgtt (SEQ ID NO:9); 5-atccagaagtgaatttacacgtgtt (SEQ ID NO:10); 5-atcccgaagtggatttacacgtgtt (SEQ ID NO:11); 5-atcccgaagtgaatttacacgtgtt (SEQ ID NO:12); 5-atcccgaagttgatttacacgtgtt (SEQ ID NO:13); and 5-atcccgaagttaatttacacgtgtt (SEQ ID NO:14); and orfRV: 5-ttgaaattctccgataatcatcac (SEQ ID NO:15); 5-ttgaaattctccgataatcctcac (SEQ ID NO:16); 5-ttgaaattctccgctaatcctcac (SEQ ID NO:17); 5-ttgaaattctccgctaatcatcac (SEQ ID NO:18); 5-ttgaaattctctataatcatcac (SEQ ID NO:19); 5-ttgaaattctcctataatcctcac (SEQ ID NO:20); 5-ttgaaattctcctctaatcatcac (SEQ ID NO:21); and 5-ttgaaattctcctctaatcctcac (SEQ ID NO$_{22}$) were synthesized. The gene was discovered by using a nucleotide probe based on the open reading frame (ORF) sequence associated with the *Bacillus popilliae* cryl 8-type genes, for example cryl 8Aa1 gene (*J. Bacteriol.* 179, 4336-4341 (1997)). These primers amplify an open reading frame associated with the cry genes of *Bacillus popilliae*. One such gene, orf1 (an orf1 gene that is not the novel orf1 gene that is a subject of the present invention), has been published in *J. Bacteriol.* 179, 4336-4341 (1997). When the PCR reaction was made with these primers and the DNA sample isolated from the *Bacillus popilliae* var. *popilliae* Hime strain used as the template, a 500-bp DNA fragment was amplified. The PCR-amplified DNA was used as the probe to identify the clone containing the new cry gene disclosed in this patent application.

Example 2

Sequence Analysis

The newly discovered *Bacillus popilliae* gene was named cryhime1. Sequencing of the cryhime1 gene and the flanking 5' and 3' regions revealed an open reading frame having some sequence homology to the cry18Aa1 orf1. BLAST search revealed that the protein encoded by cryhime1 is quite unique. The closest proteins are Cry32Aa, Cry8Aa and Cry7Aa, but they have only 36-37% identity. The protein encoded by cryhime1 was quite different from Cry18 proteins. BLAST also revealed the protein encoded by cryhime1 has a typical three-domain structure motif of Cry insecticidal proteins as described by Li et al. (*Nature* 353, 815-821 (1991)).

Example 3

Cloning and Expression in *Bacillus thuringiensis*

The cryhime1 gene was cloned in the pHY300PLK shuttle vector (Takara) with and without orf1. The cryhime1 gene was cloned in pHY300PLK as follows: Two PCR primers, 5-aagaattcgagtcgcatcgacgataatt (SEQ ID NO:1) and 5-aactgcaggtaaacgatacttttacttgtgat (SEQ ID NO:2), were made to amplify the cryhime1 gene along with its 5' and 3' flanking regions including the putative promoter and the orf1 sequence. These primers contain the EcoRI and PstI sites respectively. PCR was done using the cloned cryhime1 gene in pBluescriptSK as the template. The amplified DNA fragment was digested with EcoRI and PstI, cloned in pGEM-T Easy (Promega) and excised from the pGEM vector by EcoRI digestion. The pGEM vector provided an additional EcoRI site at the 3' end. The EcoRI fragment from pGEM was then cloned in the EcoRI site of pHY300PLK. There were two possible directions for the cryhime1 gene cloned in pHY300PLK. The clone in which the cryhime1 gene was oriented toward the same direction of the tetracycline resistant gene was selected and transferred to the Bt51 host, available from a variety of sources including the U.S. Department of Agriculture and the American Type Culture Collection.

Transformation of Bt51 was done according to the method described in *Cur. Microbiol.* 32, 195-200 (1996). The gene was highly expressed in Bt51, a cry-minus *Bacillus thuringiensis* host. Selected Bt51 transformants showing tetracycline resistance were grown for 3 days at 30° C. in flasks containing the CYS medium (ACS Symposium Series 432, 46-60, (1990)) supplemented with 5 mg/L tetracycline. After 3 day-incubation at 30° C., Bt51 produced spores and crystals and was subsequently lysed. The spores and crystals were harvested by centrifugation and analyzed by SDS-PAGE and electron-microscopy. The cryhime1 gene in Bt51 produced a protein of approximately 150 kDa that crystallized in a bipyramidal shape.

The orf1 sequence was removed from the cryhime1 gene cloned in pHY300PLK as follows: Two PCR primers, 5-cggagaatttcaattttattcactt (3' end of orf1) (SEQ ID NO:23) and 5-gtgaagcttcacgattggtgttcat (reverse and complement of 5' end of orf1) (SEQ ID NO:24), were made, and the cryhime1 gene in pHY300PLK was amplified without the orf1 sequence. The amplified fragment was self-ligated, and the sequence was confirmed. The orf1-removed cryhime1 construct was then cloned in Bt51. When Bt51 containing the orf1-deleted cryhime1 was grown in the CYS medium under the identical conditions as described for the strain carrying the cryhime1 gene with orf1, no crystals and proteins were observed by SDS-PAGE and electron-microscopy. When orf1 was deleted from the construct, no detectable expression was found. This result demonstrated that the orf1 sequence upstream from the *Bacillus popilliae* cryhime1 insecticidal gene is required for expression of the *Bacillus popilliae* insecticidal gene in *Bacillus thuringiensis* hosts.

Example 4

Bioassay

The crystals were harvested from 200 ml CYS broth by centrifugation and re-suspended in 10 ml water. An aliquot (1 ml) of the crystal suspension containing 500 micrograms protein was mixed with 5 g of sterile compost in a plastic cup containing five cupreous chafer (*Amomala cuprea*) first-instar larvae. The larvae were allowed to feed in the compost mixture for 7 days at 25° C. At the end of incubation, 6 out of 10 insects were found dead. No mortality was observed in a control experiment where no crystal was added to compost. Similar mortality was found with other Scarabaeidae species including Japanese beetle (*Popillia japonica*) and cherry chafer (*Anomala daimiana*).

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the appended claims.

What is claimed is:

1. An isolated polynucleotide comprising the sequence of SEQ ID NO:3.

2. An isolated polypeptide comprising the sequence of SEQ ID NO:5.

3. An isolated polynucleotide comprising the sequence of SEQ ID NO:4.

4. An isolated polypeptide comprising the sequence of SEQ ID NO:6.

5. The polynucleotide of claim 1 wherein said polynucleotide is operably linked to the polynucleotide of claim 3 resulting ina chimeric gene.

6. A method for constructing a recombinant *Bacillus thuringiensis* organism toxic to Scarabaeidae insects, comprising:
   (a) linking said polynucleotide sequence of claim 5 to a vector; and
   (b) introducing said chimeric gene of claim 5 linked to said vector into a *Bacillus thuringiensis* organism, wherein said chimeric gene is expressed in said *Bacillus thuringiensis* organism resulting in toxin production which is toxic to said Scarabaeidae insects.

7. A recombinant *Bacillus thuringiensis* organism made by the method of claim 6.

* * * * *

SEQUENCE LISTING

<160> NUMBER OF SEQ ID NOS: 24

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
aagaattcga gtcgcatcga cgataatt                                            28

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
aactgcaggt aaacgatact tttacttgtg at                                       32

<210> SEQ ID NO 3
<211> LENGTH: 519
<212> TYPE: DNA
<213> ORGANISM: Bacillus popilliae -continued

<400> SEQUENCE: 3

```
atgaacacca atcgtgaagc ttcactttat tatcagccag aattaccagt tcattgttcc     60
gacaaaaacc aaaaggttcc gttctgttgt gtcgtttcca ttcctcatgg atttgaaccc    120
gtagctccat ctcatcctaa gatggtatac catcttgact gcttagccac aattaaagag    180
acgtgccgca aagcggtgca agtcgaggac tgtggccatg ccgaagtcga tttacacgtg    240
ttgaaagtca aaggctgcat tccctttatc atcaatattg aagtcaaacc gaagggaaat    300
cgtgaaacat gttttactga cccgcatgcc aaagaaatct cactttgttg tgaggggagt    360
gtatgtgtag aacatgtact caaatgcagt gtcggaagtt tgccagatgt tcatatcgat    420
tgtcaatatg tgacggtatg tgatttacag atgagacccg ttcatgaggg tgcatgccaa    480
tttgtgaaga ttagcggaga atttcaattt tattcactt                           519
```

<210> SEQ ID NO 4
<211> LENGTH: 4119
<212> TYPE: DNA
<213> ORGANISM: Bacillus popilliae

<400> SEQUENCE: 4

```
taacattagc tacaaatgtt gtggctaagc accccattat ataaatggat gacaaccagg     60
aggggtaact atgaatcagt atcaacatca aaacgataac aaaagttaca atcaacatgg    120
aaatgaaatg cagatcatac aaccttcaag taattcttta ctttacagtc caaataagta    180
tccgtatgcc acggatccca atgtcatagc agagggtaga agttataata attggttgga    240
tacgtgtgta ggtgtaggcg acggtacacg aagtcccgag actgacgctg ttgctgtcgg    300
agttcgaata agccacacaa ttttccgcct actaggtgtt ccatattcag ctcaaggcga    360
gcaattattt agcttcctat tggatacgtt atggcttgaa ggcaatactc aatgggaaga    420
gttgatgaga catgcagaag aactcataaa tgaacagata ccggattatg taagaaccaa    480
ggcacttgca gaattaacgg atttaggtaa caacttaaat ttatatatag cagcttttga    540
agattggaaa cgaaatccga gcagtcaaga agttagaacc cgggtaatag atagattcaa    600
tatactcgac ggtttatttg aagcctatct gccttcattt gcagtacctg gttatgaagt    660
accactatta tccgtgtatg caaatgttgc aaatattcat ttattggtac tgagggacag    720
ctcgattcat ggtctggatt ggggattaag ttcaactagt gttgacaata attacaatcg    780
ccaacaaagg aactccgcaa cgtatgcaat tcattgtaca acttggtatc agacgggttt    840
acaaagattg caaggcagcg atgctagcag ttgggtcaat tataatcgat ttagaagaga    900
aataacgtta atagtattgg atatttgtgc attgttttca aattatgatg ttcgtagtta    960
tccaatacag ttacggggag agcttacgag aggaatttat acggatccag cagtatttag   1020
cggtacaggt tcctattcct ggttgagtca agcaccatca tttgcagaaa tagaaaatat   1080
cgcaattagg gaaccaagca attttacttg ggcaaattat gcgagagtaa caacaggtac   1140
actggaatat ctcagctcta agaatgattt ttggaaatca cactatatga actatactga   1200
aaccaattcg ggtatattga ttcaaggacc tacctatgga atgacgacgg gtacaaatat   1260
tcgtatagag tccgtatcaa tgcaagaaat ttattccgtt agattagaag ctgttgctca   1320
tgctggagct gggggtcctt ttttgggaat ctctacgtct gaatttttct ggagtttggg   1380
tgttagaagg tatcagaact cacgtagtcc tcaatttgcg tctcaaataa taactaggca   1440
attacctgga gtaaactcag cggttccatc tgccctcgac catagtcatg aactatcgta   1500
```

```
tatcacagcg tttccagcta gatcggtggg aacgattctc gttcatgaat ggacatctac   1560
aacggttagt cgtaacaata gaattgagcc agataaaata acacaaatcc cggctgttaa   1620
gtcacacaca ctctccaatt gtcaagtagt tagtgggact gggtttacgg gaggaaactg   1680
gttgagacct tctgataatg gttcatttag actaacgatt acttcattct caagccaatc   1740
ttaccgcatt cgcattcgtt atgcttccgc aacattttt tatttggata ttcgtacggg   1800
tgatacttct aacacatttg cggttacccc aacaacatta tcatcaggat cccaaactgt   1860
accctacgaa tcttttgggt ttataaatat accttatact tttacaacag cacctactga   1920
aagtagatat acttttgatt tcatgttcta ttcaatagga agcgcaaatg tattgattga   1980
ccgaattgaa tttgttccaa ttgagggttc cttgttcgag tacgaaacca acagcagct    2040 agaaaaagca aggaaagcgg tgaaccattt gtttacagat ggatcgaaaa aggcgctaaa   2100
agaagacacg accgattatg agattgatca agccgccaac gtggtagatt gtatatcgga   2160
tgagtgtgga catgagaaaa tgatcctgtt agatgaagta aaatatgcaa aacaactcag   2220
ccaagcccgc aatttactgc tcaatgggaa tttcgatgat ctatatccag ctctggagag   2280
ggagaatcca tggaaaacaa gtccgaatgt tacgatccgt cgagataacc cgattttaa   2340 aggccattat ctcagtatgg cgggtgcgaa cgatatcgag gccaccaatg ataccttccc   2400
cacgtatgtc tatcaaaaaa tagacgaagc caaattaaag ccgtatacac gttataaagt   2460
gcgcgggttt gttggcagca gcaaagctct agagctgttg gttacacgct ataatgaaga   2520
agtcgatgcg atttttagatg taccggataa tatcccgcat cgccgatac ctgtctgcgg   2580 tgaatttgat cgatgcaagc cctattcgta tccacctta cttccagaat gtaaccctga   2640
gtttataaat cagatgcaac catcctcttg ccaccacact cagatggtcg attacaataa   2700
catgaacatg agcacgagta ctaccatgaa tcctacccct acgcctgaaa tagcatccag   2760
ccaaagtgga ttcggcagaa acatcgcaa atgtcatcaa gcgcatcaat ttgagttcca   2820
tattgatacc gggacaatcg atctggtcga agatttgggc ctatgggtga tcttcaaaat   2880
ctgtgccaca gatggttacg caagcttaga tgatttggaa gtgattgaag aaggagcgct   2940
gggtgtcgaa gcattagaac ttgtcaagaa aagagaaaag aaatggagac atcagaagga   3000
gcagcactgt tcgcaaacga aacacaaata tgatgcggcc aaacatgcgg tgatggcgtt   3060
atttacaaac acgcgctatg aaaaattgaa gttcgaaaca accatctcca atattttgta   3120
tgctgatcat ctcgtgcagt cgattcctta tgtatataat aaatatgtac cggaagttcc   3180
aggtatgaat tacgaactct attcagagct aaacacactg gttcagaatg cgttctacct   3240
gtatgaccag cggaatctga ttaaaaaggg cgctttagca atgggcttat gtattggcaa   3300
gctgcccctc atgcaagagt agagcaagaa tttgagaaat cggtgctcgt gctgccaaat   3360
tgggatgcca atgtgtcgca agatctttgt atcgaacaca atcgcggtta tgtattgcgt   3420
gtcacggcga gaaaagaaga tccgggagct ggcaatgtta cctttagtga ctgtgaaaat   3480
catgtcgaca agctgagctt tacttcttgc gatatagcta caaacgcagt gccaggtgcc   3540
caagcgaatg atccagccgc cggagtagcc tatgacaac agggttgtca aatagataga   3600
gtgccgtacg ggcaatctgg atatcgagca gacggagtag cgtacgaaca gtctggtcat   3660
cgaacagatg gagtgccgta cagacaatct ggatatggaa cagacggagt aacgtacgaa   3720
caatctggtc atcgagcaga tggaatgccg tacggacaat ctggatatcg agcagatgga   3780
gtagcgtacg aacagtctgg tcatcgagca gatggagtgc cgtacggaca atctggatat   3840
ggaacagacg gagtaacgta cgaccaatct gccaatcaaa cccgcaaata tcatggttgc   3900
```

-continued

```
catacagacg gactgccaca tccagagcat ggttgttgtt atccagacag agtaagcgat   3960
ggccaacagc ttgcatatgt aacaaaatcg attgatctgt tcccggatac agataaagtc   4020
cggatcgaca ttggagaaac cgaagggaac tttagagtgg aaagtgtgga attgatttgt   4080
atggaaaagt aaatcatcac aagtaaaagt atcgtttac                          4119
```

<210> SEQ ID NO 5
<211> LENGTH: 173
<212> TYPE: PRT
<213> ORGANISM: Bacillus popilliae

<400> SEQUENCE: 5

```
Met Asn Thr Asn Arg Glu Ala Ser Leu Tyr Tyr Gln Pro Glu Leu Pro
 1               5                  10                  15

Val His Cys Ser Asp Lys Asn Gln Lys Val Pro Phe Cys Cys Val Val
            20                  25                  30

Ser Ile Pro His Gly Phe Glu Pro Val Ala Pro Ser His Pro Lys Met
        35                  40                  45

Val Tyr His Leu Asp Cys Leu Ala Thr Ile Lys Glu Thr Cys Arg Lys
    50                  55                  60

Ala Val Gln Val Glu Asp Cys Gly His Ala Glu Val Asp Leu His Val
65                  70                  75                  80

Leu Lys Val Lys Gly Cys Ile Pro Phe Ile Ile Asn Ile Glu Val Lys
                85                  90                  95

Pro Lys Gly Asn Arg Glu Thr Cys Phe Thr Asp Pro His Ala Lys Glu
            100                 105                 110

Ile Ser Leu Cys Cys Glu Gly Ser Val Cys Val Glu His Val Leu Lys
        115                 120                 125

Cys Ser Val Gly Ser Leu Pro Asp Val His Ile Asp Cys Gln Tyr Val
    130                 135                 140

Thr Val Cys Asp Leu Gln Met Arg Pro Val His Glu Gly Ala Cys Gln
145                 150                 155                 160

Phe Val Lys Ile Ser Gly Glu Phe Gln Phe Tyr Ser Leu
                165                 170
```

<210> SEQ ID NO 6
<211> LENGTH: 1340
<212> TYPE: PRT
<213> ORGANISM: Bacillus popilliae

<400> SEQUENCE: 6

```
Met Asn Gln Tyr Gln His Gln Asn Asp Asn Lys Ser Tyr Asn Gln His
 1               5                  10                  15

Gly Asn Glu Met Gln Ile Ile Gln Pro Ser Ser Asn Ser Leu Leu Tyr
            20                  25                  30

Ser Pro Asn Lys Tyr Pro Tyr Ala Thr Asp Pro Asn Val Ile Ala Glu
        35                  40                  45

Gly Arg Ser Tyr Asn Asn Trp Leu Asp Thr Cys Val Gly Val Gly Asp
    50                  55                  60

Gly Thr Arg Ser Pro Glu Thr Asp Ala Val Ala Val Gly Val Arg Ile
65                  70                  75                  80

Ser His Thr Ile Phe Arg Leu Leu Gly Val Pro Tyr Ser Ala Gln Gly
                85                  90                  95

Glu Gln Leu Phe Ser Phe Leu Leu Asp Thr Leu Trp Leu Glu Gly Asn
            100                 105                 110
```

```
Thr Gln Trp Glu Glu Leu Met Arg His Ala Glu Leu Ile Asn Glu
            115                 120                 125

Gln Ile Pro Asp Tyr Val Arg Thr Lys Ala Leu Ala Glu Leu Thr Asp
        130                 135                 140

Leu Gly Asn Asn Leu Asn Leu Tyr Ile Ala Ala Phe Glu Asp Trp Lys
145                 150                 155                 160

Arg Asn Pro Ser Ser Gln Glu Val Arg Thr Arg Val Ile Asp Arg Phe
                165                 170                 175

Asn Ile Leu Asp Gly Leu Phe Glu Ala Tyr Leu Pro Ser Phe Ala Val
            180                 185                 190

Pro Gly Tyr Glu Val Pro Leu Leu Ser Val Tyr Ala Asn Val Ala Asn
        195                 200                 205

Ile His Leu Leu Val Leu Arg Asp Ser Ser Ile His Gly Leu Asp Trp
210                 215                 220

Gly Leu Ser Ser Thr Ser Val Asp Asn Asn Tyr Asn Arg Gln Gln Arg
225                 230                 235                 240

Asn Ser Ala Thr Tyr Ala Ile His Cys Thr Thr Trp Tyr Gln Thr Gly
                245                 250                 255

Leu Gln Arg Leu Gln Gly Ser Asp Ala Ser Ser Trp Val Asn Tyr Asn
            260                 265                 270

Arg Phe Arg Arg Glu Ile Thr Leu Ile Val Leu Asp Ile Cys Ala Leu
        275                 280                 285

Phe Ser Asn Tyr Asp Val Arg Ser Tyr Pro Ile Gln Leu Arg Gly Glu
    290                 295                 300

Leu Thr Arg Gly Ile Tyr Thr Asp Pro Ala Val Phe Ser Gly Thr Gly
305                 310                 315                 320

Ser Tyr Ser Trp Leu Ser Gln Ala Pro Ser Phe Ala Glu Ile Glu Asn
                325                 330                 335

Ile Ala Ile Arg Glu Pro Ser Asn Phe Thr Trp Ala Asn Tyr Ala Arg
            340                 345                 350

Val Thr Thr Gly Thr Leu Glu Tyr Leu Ser Ser Lys Asn Asp Phe Trp
        355                 360                 365

Lys Ser His Tyr Met Asn Tyr Thr Glu Thr Asn Ser Gly Ile Leu Ile
370                 375                 380

Gln Gly Pro Thr Tyr Gly Met Thr Thr Gly Thr Asn Ile Arg Ile Glu
385                 390                 395                 400

Ser Val Ser Met Gln Glu Ile Tyr Ser Val Arg Leu Glu Ala Val Ala
                405                 410                 415

His Ala Gly Ala Gly Pro Phe Leu Gly Ile Ser Thr Ser Glu Phe
            420                 425                 430      Phe

Phe Trp Ser Leu Gly Val Arg Arg Tyr Gln Asn Ser Arg Ser Pro Gln
        435                 440                 445

Phe Ala Ser Gln Ile Ile Thr Arg Gln Leu Pro Gly Val Asn Ser Ala
    450                 455                 460

Val Pro Ser Ala Leu Asp His Ser His Glu Leu Ser Tyr Ile Thr Ala
465                 470                 475                 480

Phe Pro Ala Arg Ser Val Gly Thr Ile Leu Val His Glu Trp Thr Ser
                485                 490                 495

Thr Thr Val Ser Arg Asn Asn Arg Ile Glu Pro Asp Lys Ile Thr Gln
            500                 505                 510

Ile Pro Ala Val Lys Ser His Thr Leu Ser Asn Cys Gln Val Val Ser
        515                 520                 525

Gly Thr Gly Phe Thr Gly Gly Asn Trp Leu Arg Pro Ser Asp Asn Gly
```

-continued

```
            530                 535                 540
Ser Phe Arg Leu Thr Ile Thr Ser Phe Ser Ser Gln Ser Tyr Arg Ile
545                 550                 555                 560

Arg Ile Arg Tyr Ala Ser Ala Thr Phe Phe Tyr Leu Asp Ile Arg Thr
                565                 570                 575

Gly Asp Thr Ser Asn Thr Phe Ala Val Thr Pro Thr Thr Leu Ser Ser
                580                 585                 590

Gly Ser Gln Thr Val Pro Tyr Glu Ser Phe Gly Phe Ile Asn Ile Pro
                595                 600                 605

Tyr Thr Phe Thr Thr Ala Pro Thr Glu Ser Arg Tyr Thr Phe Asp Phe
610                 615                 620

Met Phe Tyr Ser Ile Gly Ser Ala Asn Val Leu Ile Asp Arg Ile Glu
625                 630                 635                 640

Phe Val Pro Ile Glu Gly Ser Leu Phe Glu Tyr Glu Thr Lys Gln Gln
                645                 650                 655

Leu Glu Lys Ala Arg Lys Ala Val Asn His Leu Phe Thr Asp Gly Ser
                660                 665                 670

Lys Lys Ala Leu Lys Glu Asp Thr Thr Asp Tyr Glu Ile Asp Gln Ala
                675                 680                 685

Ala Asn Val Val Asp Cys Ile Ser Asp Glu Cys Gly His Glu Lys Met
                690                 695                 700

Ile Leu Leu Asp Glu Val Lys Tyr Ala Lys Gln Leu Ser Gln Ala Arg
705                 710                 715                 720

Asn Leu Leu Leu Asn Gly Asn Phe Asp Asp Leu Tyr Pro Ala Leu Glu
                725                 730                 735

Arg Glu Asn Pro Trp Lys Thr Ser Pro Asn Val Thr Ile Arg Arg Asp
                740                 745                 750

Asn Pro Ile Phe Lys Gly His Tyr Leu Ser Met Ala Gly Ala Asn Asp
                755                 760                 765

Ile Glu Ala Thr Asn Asp Thr Phe Pro Thr Tyr Val Tyr Gln Lys Ile
                770                 775                 780

Asp Glu Ala Lys Leu Lys Pro Tyr Thr Arg Tyr Lys Val Arg Gly Phe
785                 790                 795                 800

Val Gly Ser Ser Lys Ala Leu Glu Leu Leu Val Thr Arg Tyr Asn Glu
                805                 810                 815

Glu Val Asp Ala Ile Leu Asp Val Pro Asp Asn Ile Pro His Ala Pro
                820                 825                 830

Ile Pro Val Cys Gly Glu Phe Asp Arg Cys Lys Pro Tyr Ser Tyr Pro
                835                 840                 845

Pro Leu Leu Pro Glu Cys Asn Pro Glu Phe Ile Asn Gln Met Gln Pro
                850                 855                 860

Ser Ser Cys His His Thr Gln Met Val Asp Tyr Asn Asn Met Asn Met
865                 870                 875                 880

Ser Thr Ser Thr Thr Met Asn Pro Thr Leu Thr Pro Glu Ile Ala Ser
                885                 890                 895

Ser Gln Ser Gly Phe Gly Arg Lys His Arg Lys Cys His Gln Ala His
                900                 905                 910

Gln Phe Glu Phe His Ile Asp Thr Gly Thr Ile Asp Leu Val Glu Asp
                915                 920                 925

Leu Gly Leu Trp Val Ile Phe Lys Ile Cys Ala Thr Asp Gly Tyr Ala
                930                 935                 940

Ser Leu Asp Asp Leu Glu Val Ile Glu Glu Gly Ala Leu Gly Val Glu
945                 950                 955                 960
```

```
Ala Leu Glu Leu Val Lys Lys Arg Glu Lys Lys Trp Arg His Gln Lys
                965                 970                 975

Glu Gln His Cys Ser Gln Thr Lys His Lys Tyr Asp Ala Ala Lys His
            980                 985                 990

Ala Val Met Ala Leu Phe Thr Asn Thr Arg Tyr Glu Lys Leu Lys Phe
        995                1000                1005

Glu Thr Thr Ile Ser Asn Ile Leu Tyr Ala Asp His Leu Val Gln Ser
    1010                1015                1020

Ile Pro Tyr Val Tyr Asn Lys Tyr Val Pro Glu Val Pro Gly Met Asn
1025                1030                1035                1040

Tyr Glu Leu Tyr Ser Glu Leu Asn Thr Leu Val Gln Asn Ala Phe Tyr
                1045                1050                1055

Leu Tyr Asp Gln Arg Asn Leu Ile Lys Asn Gly Arg Phe Ser Asn Gly
            1060                1065                1070

Leu Met Tyr Trp Gln Ala Ala Pro His Ala Arg Val Glu Gln Glu Phe
        1075                1080                1085

Glu Lys Ser Val Leu Val Leu Pro Asn Trp Asp Ala Asn Val Ser Gln
    1090                1095                1100

Asp Leu Cys Ile Glu His Asn Arg Gly Tyr Val Leu Arg Val Thr Ala
1105                1110                1115                1120

Arg Lys Glu Asp Pro Gly Ala Gly Asn Val Thr Phe Ser Asp Cys Glu
                1125                1130                1135

Asn His Val Asp Lys Leu Ser Phe Thr Ser Cys Asp Ile Ala Thr Asn
            1140                1145                1150

Ala Val Pro Gly Ala Gln Ala Asn Asp Pro Ala Ala Gly Val Ala Tyr
        1155                1160                1165

Gly Gln Gln Gly Cys Gln Ile Asp Arg Val Pro Tyr Gly Gln Ser Gly
    1170                1175                1180

Tyr Arg Ala Asp Gly Val Ala Tyr Glu Gln Ser Gly His Arg Thr Asp
1185                1190                1195                1200

Gly Val Pro Tyr Arg Gln Ser Gly Tyr Gly Thr Asp Gly Val Thr Tyr
                1205                1210                1215

Glu Gln Ser Gly His Arg Ala Asp Gly Met Pro Tyr Gly Gln Ser Gly
            1220                1225                1230

Tyr Arg Ala Asp Gly Val Ala Tyr Glu Gln Ser Gly His Arg Ala Asp
        1235                1240                1245

Gly Val Pro Tyr Gly Gln Ser Gly Tyr Gly Thr Asp Gly Val Thr Tyr
    1250                1255                1260

Asp Gln Ser Ala Asn Gln Thr Arg Lys Tyr His Gly Cys His Thr Asp
1265                1270                1275                1280

Gly Leu Pro His Pro Glu His Gly Cys Cys Tyr Pro Asp Arg Val Ser
                1285                1290                1295

Asp Gly Gln Gln Leu Ala Tyr Val Thr Lys Ser Ile Ala Leu Phe Pro
            1300                1305                1310

Asp Thr Asp Lys Val Arg Ile Asp Ile Gly Glu Thr Glu Gly Asn Phe
        1315                1320                1325

Arg Val Glu Ser Val Glu Leu Ile Cys Met Glu Lys
    1330                1335                1340

<210> SEQ ID NO 7
<211> LENGTH: 25
<212> TYPE: DNA
<213> ORGANISM: Artificial Sequence
<220> FEATURE:
```

-continued

```
<223> OTHER INFORMATION: Primer

<400> SEQUENCE: 7
atccagaagt ggatttacac gtgtt                                         25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
atccagaagt taatttacac gtgtt                                         25

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
atccagaagt tgatttacac gtgtt                                         25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
atccagaagt gaatttacac gtgtt                                         25

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
atcccgaagt ggatttacac gtgtt                                         25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
atcccgaagt gaatttacac gtgtt                                         25

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
atcccgaagt tgatttacac gtgtt                                         25
```

```
<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
atcccgaagt taatttacac gtgtt                                          25

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ttgaaattct ccgataatca tcac                                           24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ttgaaattct ccgataatcc tcac                                           24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ttgaaattct ccgctaatcc tcac                                           24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ttgaaattct ccgctaatca tcac                                           24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ttgaaattct cctataatca tcac                                           24

<210> SEQ ID NO 20
<211> LENGTH: 24
<212> TYPE: DNA
<213> ORGANISM: Artificial Sequence
<220> FEATURE:
<223> OTHER INFORMATION: Primer
```

-continued

```
<400> SEQUENCE: 20
ttgaaattct cctataatcc tcac                                              24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ttgaaattct cctctaatca tcac                                              24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ttgaaattct cctctaatcc tcac                                              24

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
cggagaattt caattttatt cactt                                             25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
gtgaagcttc acgattggtg ttcat                                             25
```